US012748036B2

(12) United States Patent
Kotu et al.

(10) Patent No.: US 12,748,036 B2
(45) Date of Patent: Sep. 29, 2026

(54) M-MIC: MICROFLUIDIC MICROBIOLOGICALLY INFLUENCED CORROSION MODEL

(71) Applicant: The Texas A&M University System, College Station, TX (US)

(72) Inventors: Susmitha Purnima Kotu, College Station, TX (US); Arul Jayaraman, College Station, TX (US); Mahboobul Sam Mannan, College Station, TX (US); Arum Han, College Station, TX (US)

(73) Assignee: The Texas A&M University System, College Station, TX (US)

( * ) Notice: Subject to any disclaimer, the term of this patent is extended or adjusted under 35 U.S.C. 154(b) by 686 days.

(21) Appl. No.: 16/607,787

(22) PCT Filed: Apr. 30, 2018

(86) PCT No.: PCT/US2018/030198
§ 371 (c)(1),
(2) Date: Oct. 24, 2019

(87) PCT Pub. No.: WO2018/204257
PCT Pub. Date: Nov. 8, 2018

(65) Prior Publication Data

US 2020/0217778 A1 Jul. 9, 2020

Related U.S. Application Data

(60) Provisional application No. 62/506,185, filed on May 15, 2017, provisional application No. 62/492,488, filed on May 1, 2017.

(51) Int. Cl.
*G01N 17/02* (2006.01)
*B01L 3/00* (2006.01)
(Continued)

(52) U.S. Cl.
CPC ........ *G01N 17/02* (2013.01); *B01L 3/502715* (2013.01); *C12Q 1/02* (2013.01);
(Continued)

(58) Field of Classification Search
CPC .. G01N 17/02; G01N 17/04; B01L 3/502715; B01L 2300/0645; B01L 2300/12; B01L 2300/168; C12Q 1/02
See application file for complete search history.

(56) References Cited

U.S. PATENT DOCUMENTS 5,246,560 A 9/1993 Nekoksa et al.
6,214,021 B1 * 4/2001 Hadlock ............ A61B 17/1128 606/152
(Continued)

FOREIGN PATENT DOCUMENTS

WO WO-2017018934 A1 * 2/2017 ........... G01N 27/026

OTHER PUBLICATIONS

Kotu et al. (SP Kotu, C Erbay, N Sobahi, A Han, S Mannan, A Jayaraman, Integration of electrochemical impedance spectroscopy and microfluidics for investigating microbially influenced corrosion using co-culture biofilms, NACE International Corrosion 2016 Conference Proceedings, Paper No. 7793 (2016) (Year: 2016).*
(Continued)

*Primary Examiner* — Shizhi Qian
(74) *Attorney, Agent, or Firm* — McKee, Voorhees & Sease, PLC

(57) ABSTRACT

A method for determining the susceptibility of a material to corrosion includes generating, via an inlet in a monitoring device, a laminar flow of material comprising a plurality of microorganisms. The plurality of microorganisms comprises at least one microorganism type. The method also includes forming, inside the monitoring device, in response to the laminar flow, a biofilm comprising at least one microorgan-
(Continued)

ism type. In addition, the method includes applying a voltage to the first and second electrodes during the laminar flow.

11 Claims, 10 Drawing Sheets

(51) Int. Cl.
*C12Q 1/02* (2006.01)
*G01N 17/04* (2006.01)
(52) U.S. Cl.
CPC ...... *G01N 17/04* (2013.01); *B01L 2300/0645* (2013.01); *B01L 2300/12* (2013.01); *B01L 2300/168* (2013.01)

(56) References Cited

U.S. PATENT DOCUMENTS

| | | | | |
|---|---|---|---|---|
| 2011/0259092 A1* | 10/2011 | Yu | G01N 17/02 | 73/86 |
| 2014/0048424 A1* | 2/2014 | Gu | G01N 17/02 | 204/404 |
| 2014/0080206 A1* | 3/2014 | Dahan | C12M 23/16 | 435/297.1 |
| 2015/0119286 A1* | 4/2015 | Whitfield | G01N 17/002 | 422/53 |
| 2016/0202206 A1* | 7/2016 | Goluch | G01N 33/48735 | 205/777.5 |

OTHER PUBLICATIONS

Galy et al. (O Galy, P Latour-Lambert, K Zrelli, J-M Ghigo, C Beloin, N Henry, Mapping of bacterial biofilm local mechanics by magnetic microparticle actuation, Biophysical Journal 103 (2012) 1400-1408 (Year: 2012).*

Stone et al., Engineering flows in small devices: microfluidics toward a lab-on-a-chip, Annu. Rev. Fluid Mech., 2004, 36, 381-411 (Year: 2004).*

Jin et al., Compact wireless microscope for in-situ time course study of large scale cell dynamics within an incubator, Scientific Reports, 2015, 5, 18483 (Year: 2015).*

Perez et al., Influence of *Desulfovibrio* sp. Biofilm on SAE 1018 carbon steel corrosion in synthetic marine medium, Corrosion Science, 2007, 49, 3580-3597 (Year: 2007).*

PCT/US2018/030198 International Search Report and Written Opinion dated Jul. 9, 2018 (2238-09502) (11 p.).

Galy, Olivier et al., "Mapping of Bacterial Biofilm Local Mechanics by Magnetic Microparticle Actuation," Biophysical Journal, vol. 103, No. 6, Sep. 2012, pp. 1400-1408 (2238-09502) (9 p.).

Kotu, Susmitha Purnima et al., "Integration of Electrochemical Impedance Spectroscopy and Microfluidics for Investigating Microbially Influenced Corrosion Using Co-Culture Biofilms," NACE International Corrosion 2016 Conference Proceedings, Paper No. 7793 (2238-09502) (16 p.).

Koch, Gerhardus et al., "International Measures of Prevention. Application, and Economics of Corrosion Technologies Study," NACE International Impact, Houston, TX, Mar. 1, 2016 (216 p.).

Kim, Junghyun et al., "Microfluidic Approaches to Bacterial Biofilm Formation," Molecules, vol. 17, 2012, pp. 9818-9834 (17 p.).

Hong, Seok Hoon et al., "Synthetic Quorum-Sensing Circuit to Control Consortial Biofilm Formation and Dispersal in a Microfluidic Device," Nature Communications, vol. 3, Jan. 3, 2012 (8 p.).

Lee, Joung-Hyun et al., "Microfluidic Devices for Studying Growth and Detachmentof *Staphylococcus* Epidermidis Biofilms," Biomed Microdevices, vol. 10, pp. 489-498, 2008 (11 p.).

Flemming, H.C., "Microbially influenced Corrosion of Materials: Economic and Technical Overview," Springer-Verlag Berlin Heidelberg 1996, pp. 6-14 (10 p).

Kotu, Susmitha Purnima et al., "Integration of Electrochemical Impedance Spectroscopy and Microfluidics for Investigating Microbially Influenced Corrosion using Co-Culture Biofilms," Corrosion 2016, Vancouver, British Columbia, Canada, Jul. 2016 (NACE-2016-7793) (22 p.).

* cited by examiner

M-MIC: MICROFLUIDIC MICROBIOLOGICALLY INFLUENCED CORROSION MODEL

CROSS-REFERENCE TO RELATED APPLICATIONS

This application is a 35 U.S.C. § 371 national stage application of PCT/US2018/030198 filed Apr. 30, 2018, entitled "M-MIC: Microfluidic Microbiologically Influenced Corrosion Model," which claims priority to U.S. Provisional Patent Application No. 62/492,488 filed May 1, 2017 and U.S. Provisional Patent Application No. 62/506,185 filed May 15, 2017, the disclosure of each of foregoing patent applications is hereby incorporated herein by reference in its entirety for all purposes not contrary to this disclosure.

STATEMENT REGARDING FEDERALLY SPONSORED RESEARCH OR DEVELOPMENT

Not applicable.

BACKGROUND

Microbiologically influenced corrosion (referred to herein as "MIC") is a corrosion process in which microorganisms play a significant role by actively carrying out undesirable electrochemical redox reactions on metal surfaces. MIC is a significant problem in oil and gas carrying pipelines and tanks, as well as with water pipelines relating to the chemical process industry and on ship hulls, and may lead to catastrophic failures, expensive shutdowns or expensive mitigation treatment.

SUMMARY

Embodiments of methods for determining the susceptibilities of materials to corrosion are disclosed herein. In one embodiment, a method for determining the susceptibility of a material to corrosion comprises generating, via an inlet in a monitoring device, a laminar flow of material comprising a plurality of microorganisms. The plurality of microorganisms comprises at least one microorganism type. In addition, the method comprises forming, inside the monitoring device, in response to the laminar flow, a biofilm comprising at least one microorganism type. Further, the method comprises applying a voltage to the first and second electrodes during the laminar flow.

Embodiments of devices for monitoring microbiologically influenced corrosion are disclosed herein. In one embodiment, a device for monitoring microbiologically influenced corrosion comprises a substrate. In addition, the device for monitoring microbiologically influenced corrosion comprises a first electrode mounted to the substrate. Further, the device for monitoring microbiologically influenced corrosion comprises a second electrode mounted to the substrate and oriented parallel to the first electrode. Still further, the device for monitoring microbiologically influenced corrosion comprises a top structure positioned over the first electrode and the second electrode on the substrate. The device for monitoring microbiologically influenced corrosion also comprises a microfluidic fluid channel positioned between the first electrode, the second electrode, and the top structure. The fluid channel extends from a first end to a second end.

Embodiments of devices for monitoring microbiologically influenced corrosion are disclosed herein. In one embodiment, a device for monitoring microbiologically influenced corrosion comprises an electrode disposed on a substrate. In addition, the device for monitoring microbiologically influenced corrosion comprises a top structure disposed over the electrode on the substrate to form a channel. The electrode comprises carbon steel. The channel extends from an inlet to an outlet and is configured to establish a laminar flow therein.

Embodiments described herein comprise a combination of features and advantages intended to address various shortcomings associated with certain prior devices, systems, and methods. The foregoing has outlined rather broadly the features and technical advantages of the invention in order that the detailed description of the invention that follows may be better understood. The various characteristics described above, as well as other features, will be readily apparent to those skilled in the art upon reading the following detailed description, and by referring to the accompanying drawings. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION

Figure 1:
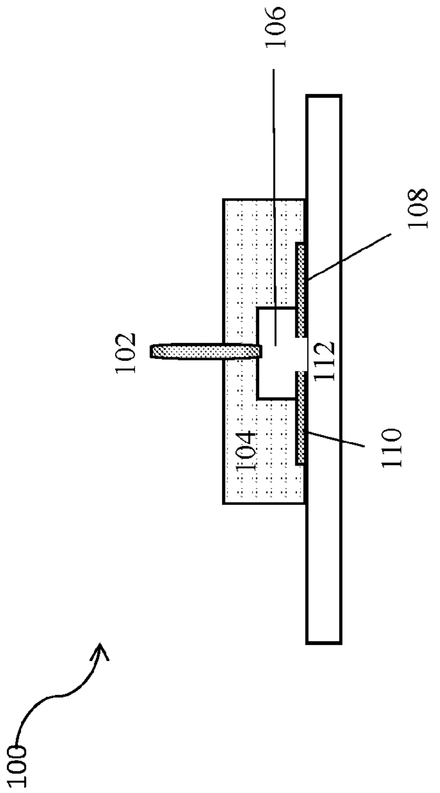
FIG. 1 is a schematic side view of an embodiment of an M-MIC in accordance with the principles described herein.

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components.

As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms “including” and “comprising” are used in an open-ended fashion, and thus should be interpreted to mean “including, but not limited to . . . .” Also, the term “couple” or “couples” is intended to mean either an indirect or direct connection. Thus, if a first device couples to a second device, that connection may be through a direct connection, or through an indirect connection via other devices, components, and connections.

Microbiologically influenced corrosion (MIC) may occur when fluid, gas, and/or solids that carry microorganisms move through or are stored in structures, or when any substrate such as, without limitation, a ship hull or other structure is in contact with the fluid, gas, and/or solid for long enough as to act as a substrate to which the microorganisms adhere. As utilized herein, “microorganism” refers to an organism that can be seen only with the aid of a microscope and that can either be unicellular or multicellular. Microorganisms (also referred to herein as “microbes”) can include bacteria, protozoans, and certain algae and fungi. As used herein, a microorganism ‘type’ can include a specific microorganism, e.g., *Vibrio natriegens*, or a broader ‘type’, such as bacteria, protozoa, etc. The adherence of microorganisms to the interior surfaces of the structures compromises the integrity of the structures. Thus, there is a need in at least the oil and gas and chemical process industry to be able to study, model, and evaluate the formation and progression of MIC, as well as the efficacy of solutions. The systems and methods disclosed herein can be utilized to analyze MIC via a continuous flow system that employs electrochemical measurements to determine corrosion while simultaneously generating a biofilm which can be subsequently analyzed to determine the offending organisms. Once identified, a corrective action (e.g., the delivery of a biocide) may be performed, and one or more subsequent analysis may be employed to determine the efficacy of the corrective action. The herein-disclosed systems and methods may thus be utilized to: (1) identify the presence of corrosion; (2) identify the extent of corrosion; (3) generate a biofilm to determine the microorganisms present to determine an appropriate corrective action; (4) analyze an effectiveness of the corrective action executed; or a combination thereof.

MIC has conventionally been analyzed using batch culture models or large scale continuous circulating loop culture models. Both currently employed batch and circulating loop systems for MIC prevention and correction experience the build-up of corrosion products and nutrient limitations in the system. However, these batch systems do not adequately represent the continuous flow environment in which MIC naturally occurs, and therefore are not desirable. Therefore, a small scale continuous flow system that better represents the conditions at which MIC occurs is desirable for studying MIC.

Herein-disclosed is a microfluidic MIC flow cell system or model (hereinafter referred to as an “M-MIC”) that can be utilized, in embodiments, to simultaneously generate information on biofilm development and corrosion. As the herein-disclosed M-MIC can be utilized to monitor microbiologically influenced corrosion, in embodiments, the M-MIC may also be referred to herein as a “monitoring device”. “Microfluidics” refers to the science of studying the behavior of fluids through micro-channels, for example, manipulating and controlling fluids in the range of microliters ($10^{-6}$) to picoliters ($10^{-12}$) flowing in a channel with dimensions in a range of from tens to hundreds of micrometers. For example, in embodiments, microfluidic indicates that the herein-disclosed M-MIC comprises a flow cell or channel through which fluid flows that has a height and width (for flow paths or channels having rectangular or square cross sections) or a diameter (for flow paths or channels having cylindrical cross sections), but not necessarily a length, that is less than or equal to about 5000, 4000, 3000, 2000, or 1000 micrometers (μm). In embodiments, the herein-disclosed systems and methods integrate biofilm characterization with electrochemical measurements, using real-time dynamic measurements, to determine the presence and/or extent of corrosion as well as the type and permeation of microorganisms. In particular, the herein-disclosed systems and methods are directed towards an M-MIC fabricated by creating a pair of metal electrodes on a glass substrate. In an embodiment, the electrodes may comprise different materials such as steel and/or titanium. In embodiments, a first electrode may comprise a first material and may be configured parallel to and separated from a second electrode by a channel (e.g., a negative space). The channel can be a microfluidic flow channel having a width and height or a diameter that is less than or equal to about 5000, 4000, 3000, 2000, 1000, or 500 μm. For example, in embodiments, the channel may have a width of about 1000 μm, and/or a height of about 500 μm. The channel may have a length that is substantially larger than (e.g., greater than or equal to about 2, 3, 4, 5, 6, 7, 8, 9, 10, or 15 times) the width and/or the height thereof, in embodiments. For example, in embodiments, the channel length is greater than or equal to about 2, 3, 4, 5, 6, 7, 8, 9, or 10 mm. In embodiments, the channel has a dimension along a direction of fluid flow from an inlet (or first side) to an outlet (or second side) that is at least 2, 3, 4, 5, 6, 7, 8, 9, 10, or 15 times a dimension of the channel in a direction perpendicular to the fluid flow from the inlet (or first side) to the outlet (or second side), and the dimension of the channel in the direction perpendicular to the fluid flow is less than or equal to about 5000, 4000, 3000, 2000, 1000, or 500 μm.

The first and the second electrodes can be made from the same material or differing materials, depending upon the application. In embodiments, a first electrode comprises a test material (e.g., a target for the biofilm to form on) and a second electrode comprises a non-corroding material. In such embodiments, the second electrode may be referred to as the “counter electrode.” In embodiments, the first electrode comprises a test material such as, without limitation, SAE 1018 carbon steel. In embodiments, the second electrode comprises a non-corroding material such as, without limitation, titanium. The biofilm formed via the M-MIC may be employed for analysis instead of or in addition to conventionally used samples that may be scraped from a target. In an embodiment, a gas-permeable polymer microfluidic channel structure placed on top of the electrode pair allows cells to be seeded and cultured directly on top of this electrode pair while allowing continuous perfusion to the cells to allow them to form a biofilm on top of the electrodes. This M-MIC configuration can allow microbe-driven corrosion to be monitored directly using, for example, electrochemical impedance spectroscopy (EIS) between the two electrodes. Alternatively or additionally, in embodiments, the gas-permeable polymer microfluidic channel structure comprises an optically transparent polymer. 'Transparent' polymer indicates that the microbial community and biofilm growth can be directly monitored and/or visualized using, for example, three dimensional biofilm structures obtained from confocal laser scanning microscopy. Confocal microscopy (e.g., confocal laser scanning microscopy or CLSM) is an imaging method that uses laser scanning to increase optical resolution and contrast of a micrograph to obtain three-dimensional images, the microscope reads, sees, and/or evaluates depth levels of a sample individually and sequentially to obtain images. As discussed herein, the M-MIC enables integration of microbe/biofilm-driven electrochemical corrosion mechanisms occurring at the metal surface with the biofilm characteristics on the surface.

Embodiments of the herein-disclosed M-MIC can be used to non-destructively and simultaneously monitor microbial biofilm development on metal surfaces of interest, as well as the changes in electrochemical parameters using electrochemical impedance spectroscopy, in real-time, which allows monitoring of the extent of corrosion of the metals. The herein-disclosed M-MIC may be applicable in studies with either or both field samples and laboratory experiments. Via the herein-disclosed M-MIC, field samples from MIC sites, such as, without limitation, water samples or biofilm scrapings from pipelines or sites impacted with MIC can be used to replicate the test environment in the lab and characterize MIC in terms of biofilm biomass, electrochemical changes, hydrodynamic parameters, and/or surface modifications, all in real-time. In embodiments, the herein-disclosed M-MIC can alternatively or additionally be used to culture MIC-relevant biofilms to determine the optimum biocide combination and dosage for attenuating and/or eradicating MIC prior to initiating a biocide application or treatment. Furthermore, the effectiveness of new biocide formulations can be tested against that of known biocides to determine the efficiency of the new biocides by analyzing the above-mentioned parameters via the herein-disclosed M-MIC.

The use of microfluidic flow cells to simultaneously generate information on biofilm development and corrosion in a condition that is similar to a real/natural setting is desirable and is enabled by the herein-disclosed M-MIC, as microbial community formation and electrochemical reactions together contribute to MIC. In addition, in embodiments, the herein-disclosed M-MIC provides the ability to carry out dynamic measurements and obtain information on corrosion processes, biofilm characteristics, or biocide efficacy in real-time. Typically, MIC is characterized using end-point measurements of either surface changes (e.g., using weight loss or scanning electron microscopy (SEM)) or microbial community composition. Different MIC sites are characterized by uniquely different microbial composition and activity, so developing a broadly applicable biocide may not be an option because different microorganisms may exhibit different degrees of tolerance to biocides. In an embodiment, the herein-disclosed M-MIC may be used to tailor the biocide composition and/or dose to the microbial community present in a target site prior to initiating mitigation strategies, thereby avoiding the use of biocide(s) or mitigation strategies that may not be effective. Thus, in embodiments, utilization of the herein-disclosed M-MIC can help in the identification and application of appropriate corrective actions more quickly than using conventional systems.

The herein-disclosed M-MIC can be used to simultaneously monitor microbial biofilm development on metal surfaces of interest, as well as the changes in electrochemical parameters (e.g., that indicate corrosion) using techniques including, but not limited to, electrochemical impedance spectroscopy (EIS) and open circuit potential. In embodiments, the herein-disclosed M-MIC comprises a two electrode system wherein the non-corroding counter electrode can comprise titanium and the corroding working electrode can comprise carbon steel 1018 grade. In alternate embodiments, the electrode or electrodes of the herein-disclosed M-MIC may comprise a non-corroding counter electrode comprising other non-corroding metals, such as, for example, silver and/or gold, and a corroding working electrode comprising corroding metals and/or alloys such as, for example, iron, other grades of steels, aluminum, zinc, copper, etc., or alloys and combinations thereof.

FIG. 1 is a schematic side view of an embodiment of an M-MIC 100 according to embodiments of the present disclosure. In this embodiment of M-MIC 100, a first electrode 108 and a second electrode 110 are disposed parallel and not in contact with each other on a substrate 112. A structure 104 is formed in contact with a portion of the substrate 112 and in contact with at least a portion of each of the first 108 and second 110 electrodes such that a channel 106 is formed in a negative space between the first electrode 108 and the second electrode 110 and the structure 104. The channel 106 comprises an inlet and an outlet (not shown here but shown in FIG. 3 below), each of which is in fluid communication with tubing 102. In an embodiment, the M-MIC 100 is disposed in a continuous flow system, where gas, liquid, solids, and/or combinations thereof are introduced to the fluid channel 106 via the inlet such that a laminar flow is established. In embodiments, flow rates in the range of from 0.10 mL/h to 2 mL/h, from 0.10 mL/h to 1 mL/h, or from 0.10 mL/h to 2 mL/h or more may be used, depending upon the size of the fluid channel 106 and other factors. As used herein, "laminar" indicates fluid flow of a liquid in which layers glide over one another, e.g., streamline fluid flow in which a fluid flows in parallel layers, with little or no disruption between the layers.

In an embodiment, a biofilm may form on at least the first electrode 108 after a predetermined period of use/flow. This biofilm may be analyzed in the device or extracted to determine a composition of the biofilm, including which microorganisms are present and/or in what concentration they are present. In embodiments, the substrate 112 comprises glass, the structure 104 comprises polydimethylsiloxane (PDMS), the first (or corroding working) electrode 108 comprises steel, the second (or counter) electrode 110 comprises titanium, and the tubing 102 comprises a polymer. In embodiments, the first 108 and second 110 electrodes comprise a corroding metal, such as, for example, steel. In embodiments, such as embodiments for which no biofilm formation is desired and the device is rather used for corrosion measurement/determination, both electrodes 108 and 110 may be non-corroding electrodes, such as, without limitation, titanium.

Figure 2:
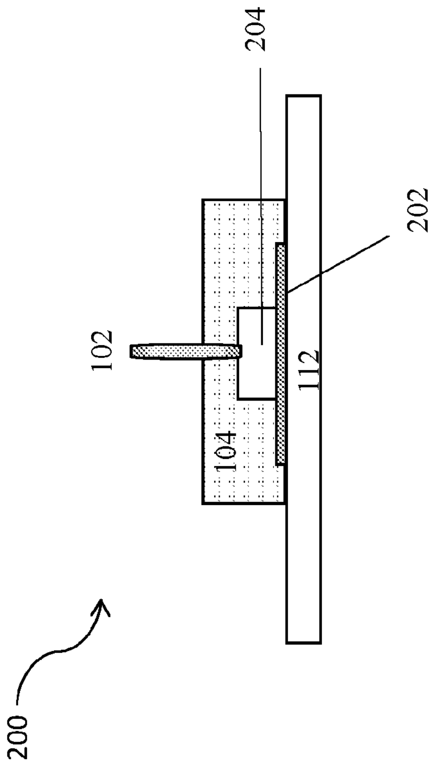
FIG. 2 is a schematic side view of an embodiment of an M-MIC in accordance with the principles described herein.

FIG. 2 is a schematic side view of an alternate embodiment of an M-MIC 200 according to certain embodiments of the present disclosure. In such embodiments, the M-MIC 200 can also be used to culture MIC-relevant biofilms from various samples to determine the optimum biocide combination and/or dosage required for attenuating MIC prior to initiating biocide application or treatment. For such applications, an evaluation of biofilm kill studies can be performed via the M-MIC 200. M-MIC 200 comprises a single electrode 202, in contrast with the two electrodes of M-MIC 100 of FIG. 1. In the M-MIC 200, an electrode 202 is formed on a substrate 112. A structure 104 is formed in contact with a portion of the substrate 112 and in contact with at least a portion of the electrode 202 such that a channel 204 is formed in a negative space in between the electrode and the structure 104. The channel 204 comprises an inlet and an outlet (not shown here but shown in FIG. 3 below), each of which is in fluid communication with tubing 102. In an embodiment, the M-MIC 200 is disposed in a continuous flow system, where gas, liquid, solids, and/or combinations thereof flow from the inlet to the outlet along the channel 204 such that a biofilm forms on the electrode 202 after a predetermined period of use. The formed biofilm may be analyzed in the M-MIC 200 device or extracted therefrom to determine a composition of the biofilm, including which microorganisms are present and/or in what concentration the microorganisms are present. In embodiments, the substrate 112 comprises glass, the structure 104 comprises PDMS, the electrode 202 comprises steel, and the tubing 102 comprises a polymer. In such embodiments, since the entire channel 204 is deposited only with one metal, e.g., carbon steel, the M-MIC may be used to evaluate biocides to determine a dosage and resulting efficiency by analyzing the metabolic state of the biofilm (using, for example, confocal microscopy) both before and after biocide treatment(s) is delivered.

Figure 3:
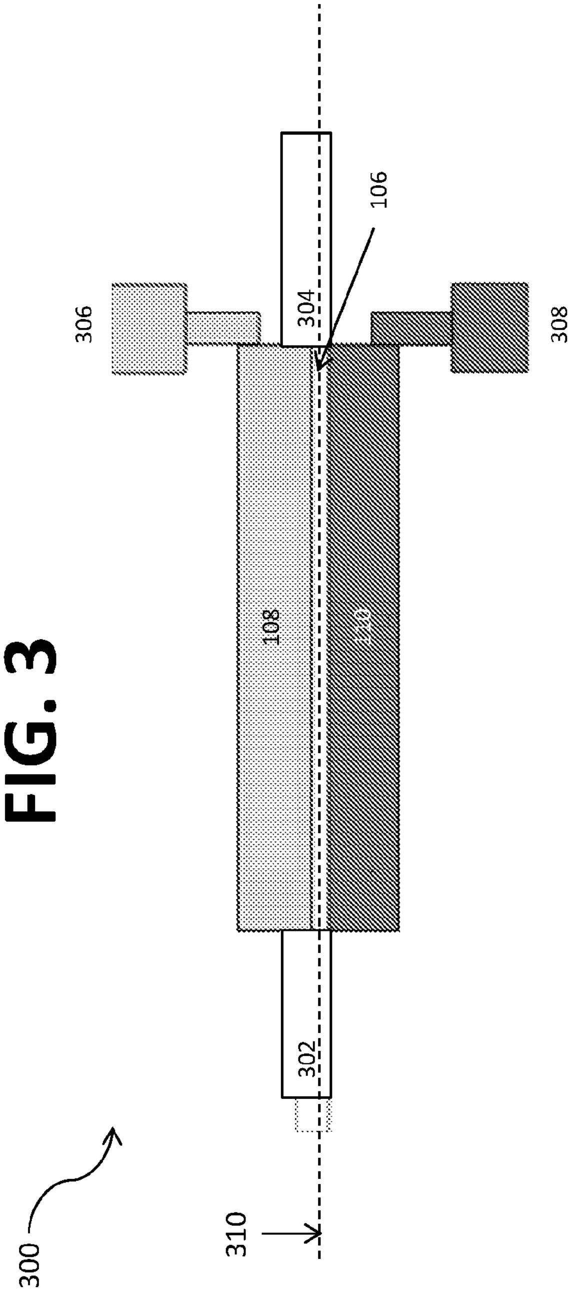
FIG. 3 is a top view of the M-MIC of FIG. 1.

FIG. 3 is a top view 300 of the M-MIC 100 of FIG. 1. In FIG. 3, the top view depicts the first electrode 108 disposed parallel to and not in contact with the second electrode 110. A central axis 310 is aligned with the channel 106, the channel 106 extends from an inlet 302 to an outlet 304, and laminar flow is established from the inlet 302 to the outlet 304 via a pump, as illustrated and discussed hereinbelow with reference to FIG. 4. The first electrode 108 is coupled to a (first) contact 306 and the second electrode 110 is coupled to a second contact 308. The substrate 112 and top structure 104 are not illustrated in FIG. 3 for ease of illustration purposes, but it is to be understood that, just as in FIG. 1, the first electrode 108 and the second electrode 110 are disposed on a (e.g., glass) substrate 112 and that the channel 106 is formed in part by the structure 104.

Figure 4:
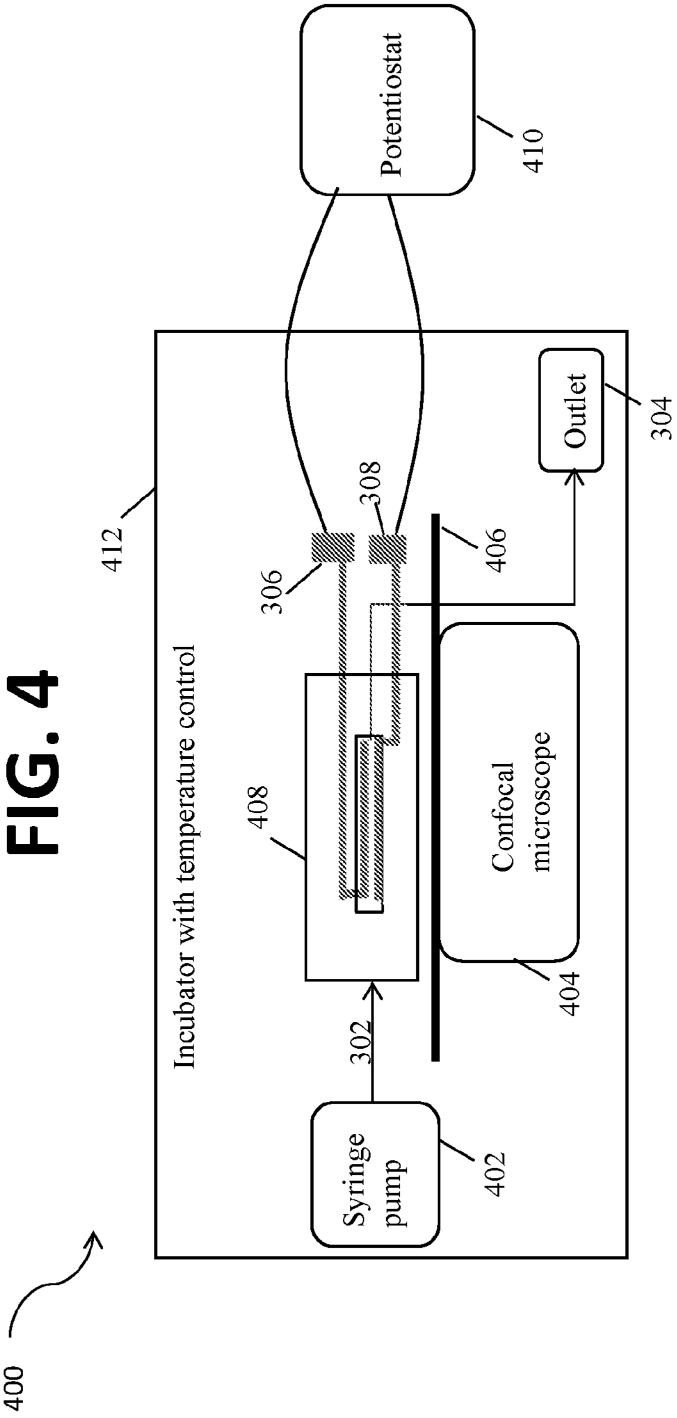
FIG. 4 is an example experimental setup 400 of an M-MIC according to an embodiment of this disclosure.

FIG. 4 is an exemplary experimental setup 400 of an M-MIC. In the example setup 400, an incubator 412 is utilized. A syringe pump 402 is coupled to the M-MIC inlet 302, which is in fluid communication with the M-MIC 408 via the channel (not shown but illustrated in FIGS. 1-3 above). While the M-MIC 408 shown in FIG. 4 is a two-electrode structure similar to FIGS. 1 and 3, it is to be understood that, in embodiments, the aforementioned single electrode structure, such as M-MIC 200 from FIG. 2, may be employed as well. A potentiostat or other controllable voltage/power source 410 is coupled to the first contact 306 and the second contact 308 and configured to apply a voltage to generate a current. The current generated may be measured to obtain an impedance variation which may be used to measure corrosion on the one or more electrodes of the M-MIC 408. In embodiments, a confocal microscope 404 is removably coupled to a base 406 on which the M-MIC 408 rests. The syringe pump 402 introduces a flow of material into the channel of the M-MIC 408 at a low flow rate such that a biofilm that may be further analyzed forms in the M-MIC 408. Once a determination is made as to the composition of the biofilm formed, a biocide may be introduced via the inlet 302, and the confocal microscope 404 may be employed to capture images both before and after the introduction of the biocide in order to determine the efficacy of the biocide employed. This information may be stored in a database and further analyzed to determine best practices for the identification and elimination of microorganisms.

Embodiments of M-MICs disclosed herein (e.g., M-MIC 100, 200) can be formed via any methods known in the art or to be discovered. A herein-disclosed method of manufacturing embodiments of M-MICs disclosed herein comprising a glass slide substrate with patterned metal electrodes will be described in detail with reference to FIG. 10 in Example 3 hereinbelow. The patterning of the metal layers described below can be effected, in embodiments, via photolithography. As described in detail with reference to FIG. 10 in Example 3 hereinbelow, such a method 1100 can comprise cleaning a substrate (e.g., a glass slide) 1102, depositing a non-corroding metal (e.g., titanium) on a cleaned substrate (e.g., the cleaned glass slide) 1104, spin coating a photoresist layer for a spin coat time 1106, exposing to ultraviolet (UV) light in the presence of a mask aligner for a UV exposure time 1108, developing the photoresist for a developing time 1110, wet etching 1112, removing the photoresist 1114, spin coating a second photoresist layer 1116, exposing to ultraviolet (UV) light in the presence of a mask aligner for a second UV exposure time 1118, developing the photoresist for a second developing time 1120, depositing corroding metal (e.g., steel) using metal sputter 1122, removing photoresist 1124, or a combination thereof. The various steps can be performed in any suitable order, combined, duplicated or absent, in embodiments. Each step can be performed as known in the art, or as specifically described hereinbelow.

Cleaning a substrate 1102 can be performed in any manner known in the art, for example, cleaning with piranha solution (a 4:1 vol/vol mixture of sulfuric acid and hydrogen peroxide) used to clean organic residues off substrates for a cleaning time of, for example, 10 minutes and/or with a 1:100 hydrofluoric acid (HF) solution for a time of, for example, 30 seconds. The substrate can comprise, for example, a glass slide. The slide may have any suitable dimensions, for example, 2 inches (5.08 cm) by 3 inches (7.62 cm) and 1.1 mm thick.

Depositing a non-corroding metal (e.g., titanium) on a cleaned substrate (e.g., the cleaned glass slide) 1104 can comprise, for example, depositing non-corroding metal on the substrate using a metal evaporator.

Spin coating a photoresist layer for a spin coat time 1106 can comprise spin coating with a photoresist such as photoresist S1818 for a spin coat time of, for example, 30 seconds at a rotation rate of, for example, 4000 revolutions per minute (RPM).

Exposing to ultraviolet (UV) light in the presence of a mask aligner for a UV exposure time 1108 can comprise, for example, exposing the slide to UV along with a photomask for a UV exposure time of, for example, 20 seconds.

Developing the photoresist for a developing time 1110 can comprise, for example, developing the slide in a developing solution such as, for example, AZ 726 MIF, for a developing time of, for example, 45-60 seconds.

Wet etching (e.g., of titanium) 1112 can be performed, for example, using an aqueous solution of HF (e.g., a 2:100 solution of HF to deionized (DI) water).

Removing the photoresist 1114 can comprise, for example, immersing the slide in acetone for a removal time of, for example, 5 minutes.

Spin coating a second photoresist layer 1116 can comprise a lift-off method to obtain the pattern desired for the working (e.g., steel) electrode after the non-corroding electrode has been deposited, patterned, and etched. In the lift-off method, spin coating a second photoresist layer 1116 comprises using a photoresist pattern as a liftoff mold and disposing the photoresist on the substrate via spin coating at 1116.

Exposing to ultraviolet (UV) light in the presence of a mask aligner for a second UV exposure time 1118 can comprise, for example, employing a photomask and exposing the structure to UV in a mask aligner.

Developing the photoresist for a second developing time 1120 can comprise, for example, developing as described in developing the photoresist for a developing time 1110.

Depositing corroding metal (e.g., steel) using metal sputter 1122 can comprise, for example, depositing SAE 1018 carbon steel as the working electrode utilizing metal sputtering.

Removing photoresist 1124 can comprise, for example, removing the photoresist via dissolution and/or otherwise to obtain the working electrode, completing the electrode pair having different materials (e.g., the non-corroding, titanium, counter electrode and the corroding, steel working electrode). The electrodes can have any suitable size. For example, in embodiments, the width of each of the counter and working electrodes is in a range of from about 0.2 to about 0.6 mm, from about 0.3 to about 0.5 mm, from about 0.4 to about 0.6 mm, or less than or equal to about 0.2, 0.25, 0.3, 0.35, 0.4, 0.45, 0.5, 0.55, 0.6, 0.65, or 0.7 mm. The gap between the counter and working electrodes can be any suitable size, such as, for example, in a range of from about 0.05 to about 0.2 mm, from about 0.07 to about 0.15 mm, from about 0.07 to about 0.12 mm, or less than or equal to about 0.05, 0.06, 0.07, 0.08, 0.09, 0.10, 0.11, 0.12, 0.13, 0.14, or 0.15 mm.

The glass slide with patterned metal electrodes obtained at 1124 can be bonded to a microchannel structure. The microchannel structure can comprise a PDMS microchannel structure, in embodiments. In such embodiments, the method can further comprise forming the microchannel structure, and bonding the patterned glass slide and PMDS structure layers to form the M-MIC. The bonding may be effected via any suitable methods, such as, without limitation, oxygen plasma treatment.

Forming the microchannel structure can comprise, for example, mixing a silicone elastomer and a curing agent (e.g., in a ratio of 10:1) and pouring the mixture onto a 3-dimensional (3D) printed mold with ridge structure (which is the inverse of the microchannel structure). The rectangular ridge structure and/or microchannel structure may be any suitable dimensions, for example, 1000 μm in width, 10 mm in length, and/or 500 μm in height. The microchannel structure (e.g., PMDS microchannel structure) can be formed in the inverse microchannel structure and peeled after curing, to provide the structure 104.

Tubing, such as Tygon tubing, can be utilized for fluidic connections of inlets and outlets to the syringes (e.g., inlet 302, outlet 304, tubing 102). The tubing may have any suitable dimensions, such as, without limitation, 0.01 inch (0.25 mm) inner diameter (ID) and 0.03 inch (0.76 mm) outer diameter (OD). A syringe pump 402 may be utilized to obtain continuous flow, as depicted in FIG. 4. Wires (e.g., copper wires of 24 gauge) may be attached to electrode pads for the contacts (e.g., first contact 306 and second contact 308 of the embodiment of FIG. 3) by any suitable methods. For example, silver paste may be utilized to attach wires to the electrode pads for the contacts 306 and 308. In embodiments, epoxy may be utilized to prevent the wires from subsequent unintentional decoupling.

EXAMPLES

The embodiments having been generally described, the following examples are given as particular embodiments of the disclosure and to demonstrate the practice and advantages thereof. It is understood that the examples are given by way of illustration and are not intended to limit the specification or the claims in any manner.

Example 1: Growing Biofilms in Two Electrode System of FIGS. 1 and 3 with *V. natriegens*

FIGS. 5-8 graphically illustrate data obtained by growing biofilms in the two electrode system (such as M-MIC 100 described with reference to FIGS. 1 and 3) with a model biofilm former, *Vibrio natriegens* also identified to cause MIC. In this Example 1, the corroding working electrode comprised steel and the counter electrode comprised titanium. The substrate 112 comprised glass, and the structure 104 comprised PDMS. *V. natriegens* was modified to express green fluorescent proteins to allow imaging biofilms grown on metal. A flow rate of 0.25 mL/h was used to supply growth media to the growing biofilm. Because low flow rates are employed in the systems and methods discussed herein, comparatively small samples of material may be used. In alternate embodiments, flow rates in the range of from 0.10 mL/h to 2 mL/h, or from 0.10 mL/h to 0.75 mL/h or more may be used, depending upon the size of the channel and other factors. In this example, the confocal microscopy images and electrochemical impedance spectroscopy data were both taken at a 3 hour time point.

Figure 5:
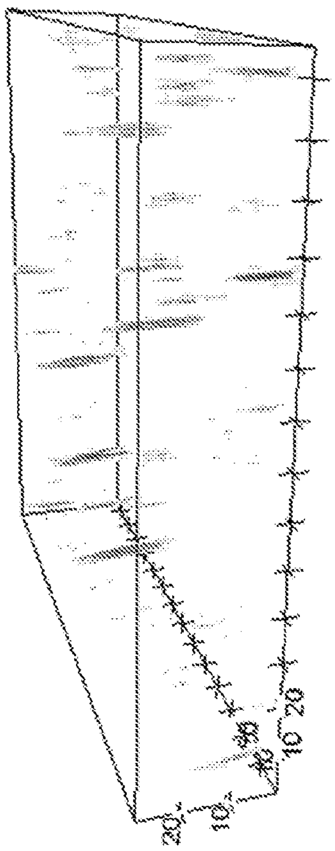
FIG. 5 is a three-dimensional image of a biofilm of *Vibrio natriegens;*

FIG. 5 is a three-dimensional image of a biofilm of *Vibrio natriegens* with the biofilm biomass recolored in gray. Leica TCS SP8-RS Confocal Laser Scanning Microscope was used for taking biofilm images. A 488 nm Argon laser was used for visualizing green fluorescent bacteria. Images were taken with a 20× objective at five different locations on the carbon steel surface spanning the length of the channel of the M-MIC. Z-stacks were taken at every 2.5 μm distance. The confocal microscopy images were processed and quantified with an image processing software, Comstat2. At 3 hours, the biomass was calculated to be 12.8±0.85 $\mu m^3/\mu m^2$. VERSASTAT3 from Princeton Applied Research was used for all EIS measurements. An input AC voltage signal of 10 mV was used over the frequency range of 100 kHz to 10 mHz to record the impedance measurements. The impedance was measured across the working and counter electrodes. Potential difference was also measured across the two electrodes and the system showed a potential difference of 50 mV across the two electrodes.

Figure 6:
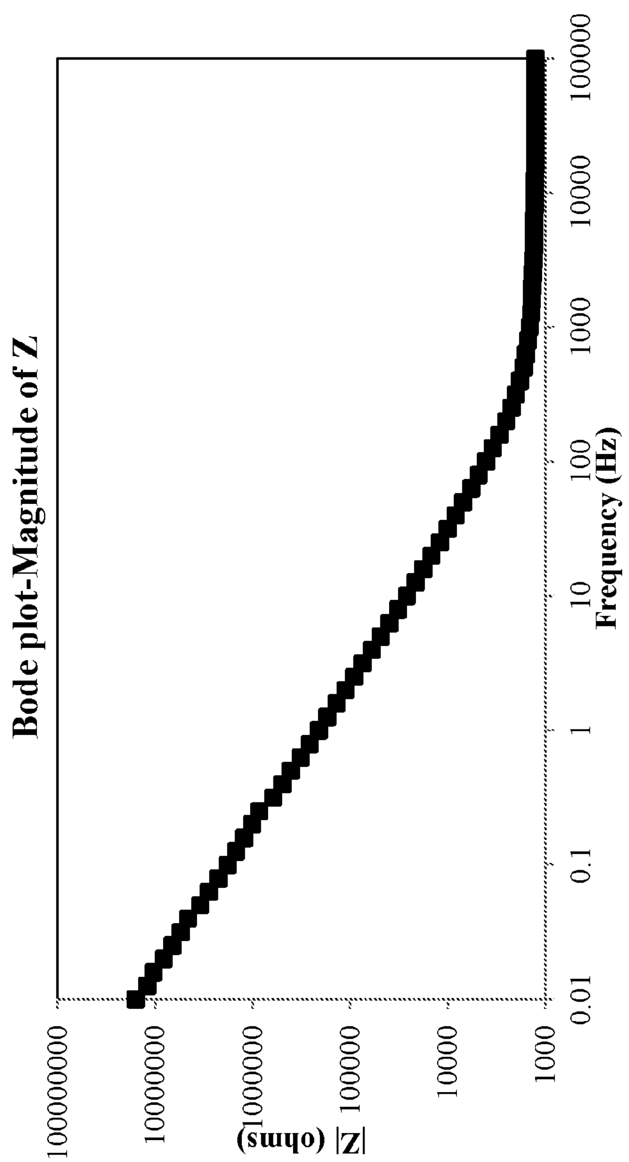
FIG. 6 is a Bode plot (|Z| vs. frequency) of *V. natriegens* biofilm at a 3 hour time point.
Figure 7:
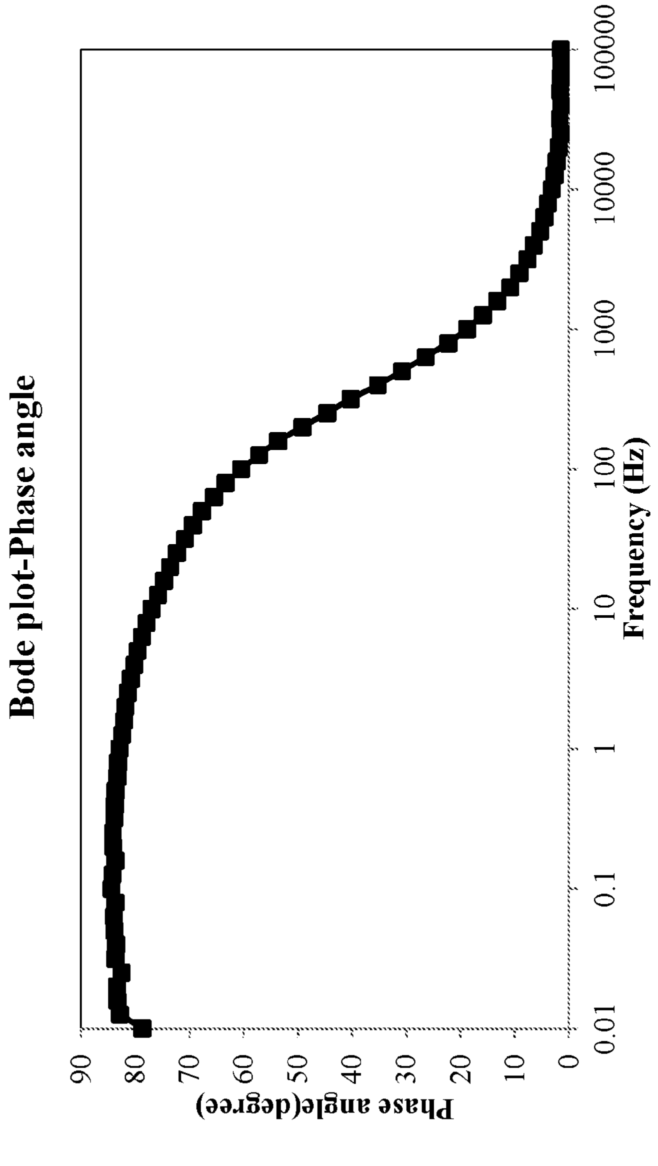
FIG. 7 is a Bode plot (phase angle vs. frequency) of *V. natriegens* biofilm at 3 hour time point.
Figure 8:
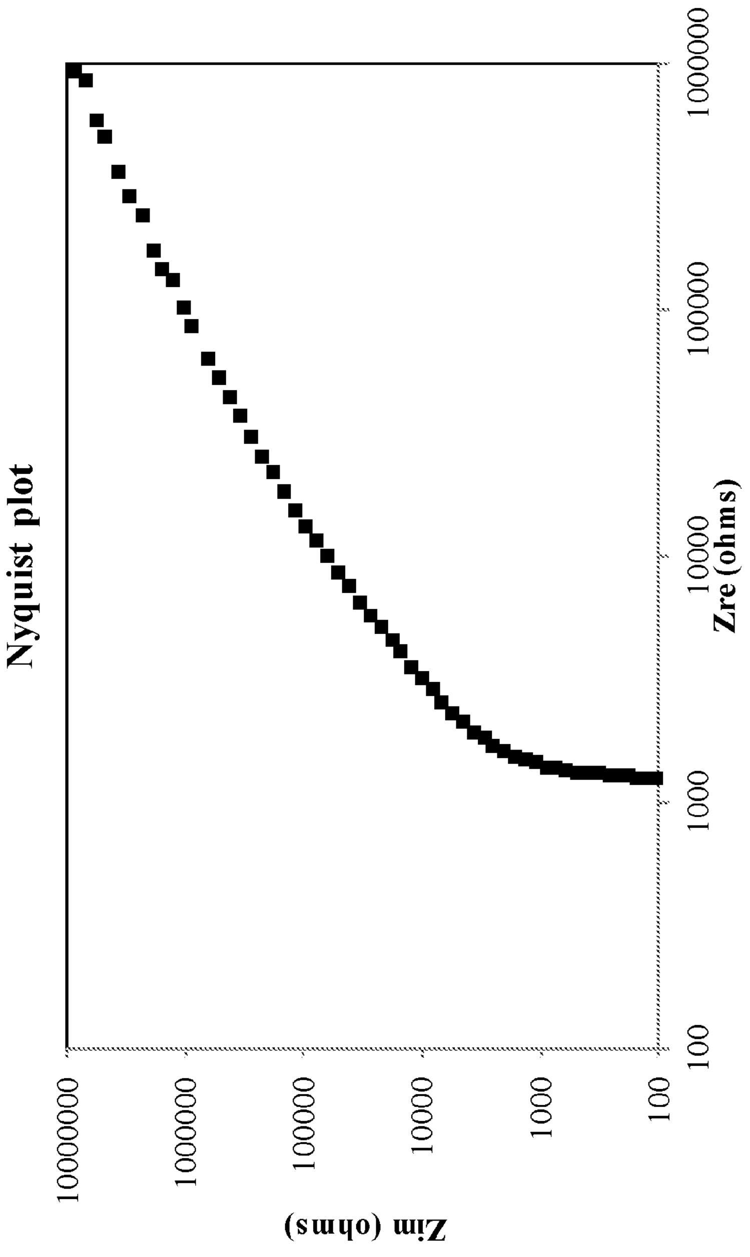
FIG. 8 is a Nyquist plot (Zim vs. Zre) of *V. natriegens* biofilm at 3 hour time point.

FIG. 6 is a Bode plot (|Z| vs. frequency, wherein |Z| is the modulus of impedance) of *V. natriegens* biofilm at a 3 hour time point and FIG. 7 is a Bode plot (phase angle of impedance vs. frequency) of *V. natriegens* biofilm at 3 hour time point. FIG. 8 is a Nyquist plot (Zim vs. Zre, wherein Zim is the imaginary component of impedance comprising of capacitive and inductive components of a circuit and Zre is the real component of impedance comprising of resistive components of a circuit) of *V. natriegens* biofilm at 3 hour time point. In potentiostatic EIS, as used herein and depicted in FIG. 4, alternating low voltage is applied to the system and the current is measured to give the impedance. Bode plots (FIGS. 6 and 7) represent the absolute impedance of the system along with the phase angle across the different frequencies swept. Nyquist plots (FIG. 8) represent the imaginary impedance with the real impedance. Using the data from Bode and Nyquist plots, an electrochemical system can be fitted to an equivalent circuit of resistors and/or capacitors based on the nature of the system. As known in the art, these plots and equivalent circuit fitting can be utilized to obtain the polarization resistance that can be related inversely to the corrosion current and the corrosion rate of the system. In addition, the potential difference between the working and reference electrodes can be used as a qualitative measure of the extent of corrosion.

Example 2: Growing *Shewanella oneidensis* Biofilm in Single Electrode System of FIG. 2

Figure 9:
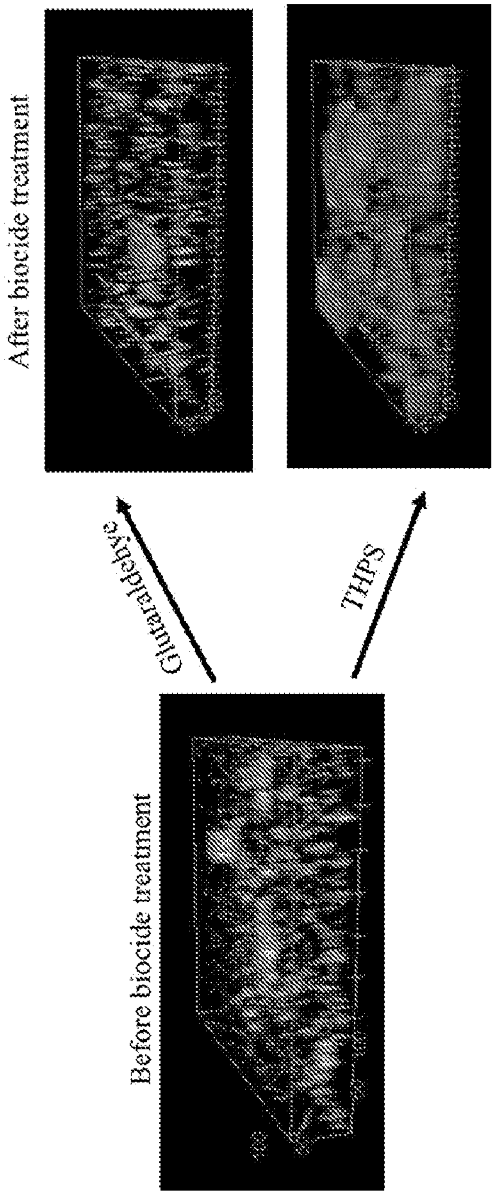
FIG. 9 is a 3D view of *S. oneidensis* biofilms grown for 12 hours on carbon steel before (left) and after (right) biocide treatment with glutaraldehyde or THPS.

Biofilms of *Shewanella oneidensis* (e.g., *S. oneidensis*, an iron-reducing bacterium commonly found in MIC sites) were grown on carbon steel in the single-metal system, such as M-MIC 200 as depicted in FIG. 2. In this Example 2, the single electrode comprised steel, the substrate 112 comprised glass, and the structure 104 comprised PDMS. Biofilms were developed in the system at 30° C. with a constant flow of Luria-Bertani growth medium which contained 10 g/l tryptone, 5 g/l yeast extract and 15 g/l sodium chloride being introduced at a flow rate of 0.25 mL/h. After 12 hours, flow of growth medium was stopped and 400 ppm of two common oilfield biocides, glutaraldehyde and tetrakis-hydroxymethyl-phosphonium sulfate (THPS), were added to the biofilms. After 4 hours, live and dead cells in the biofilms were stained using SYTO9 (green) and propidium iodide (red), respectively. Stained biofilms were analyzed for the percentage of live and dead cells to determine biocide efficiency. FIG. 9 shows the difference in the biofilm viability when treated with the two biocides. A 2.1-fold increase in the percentage of dead cells was observed with glutaraldehyde treatment while the percentage of dead cells with THPS treatment increased by 3.1-fold. This data suggests that THPS treatment is more effective than glutaraldehyde against *S. oneidensis* biofilms under the conditions tested. In addition to determining the right biocide, similar studies can be conducted with different biocide concentrations to also determine the appropriate biocide dosage. The herein-disclosed M-MIC flow system and method enable the conducting of biocide efficacy studies in the laboratory to decide the effective biocide dosage to be applied in the field for effective MIC mitigation.

Example 3: Method of Manufacturing a Herein-Disclosed M-MIC

Figure 10:
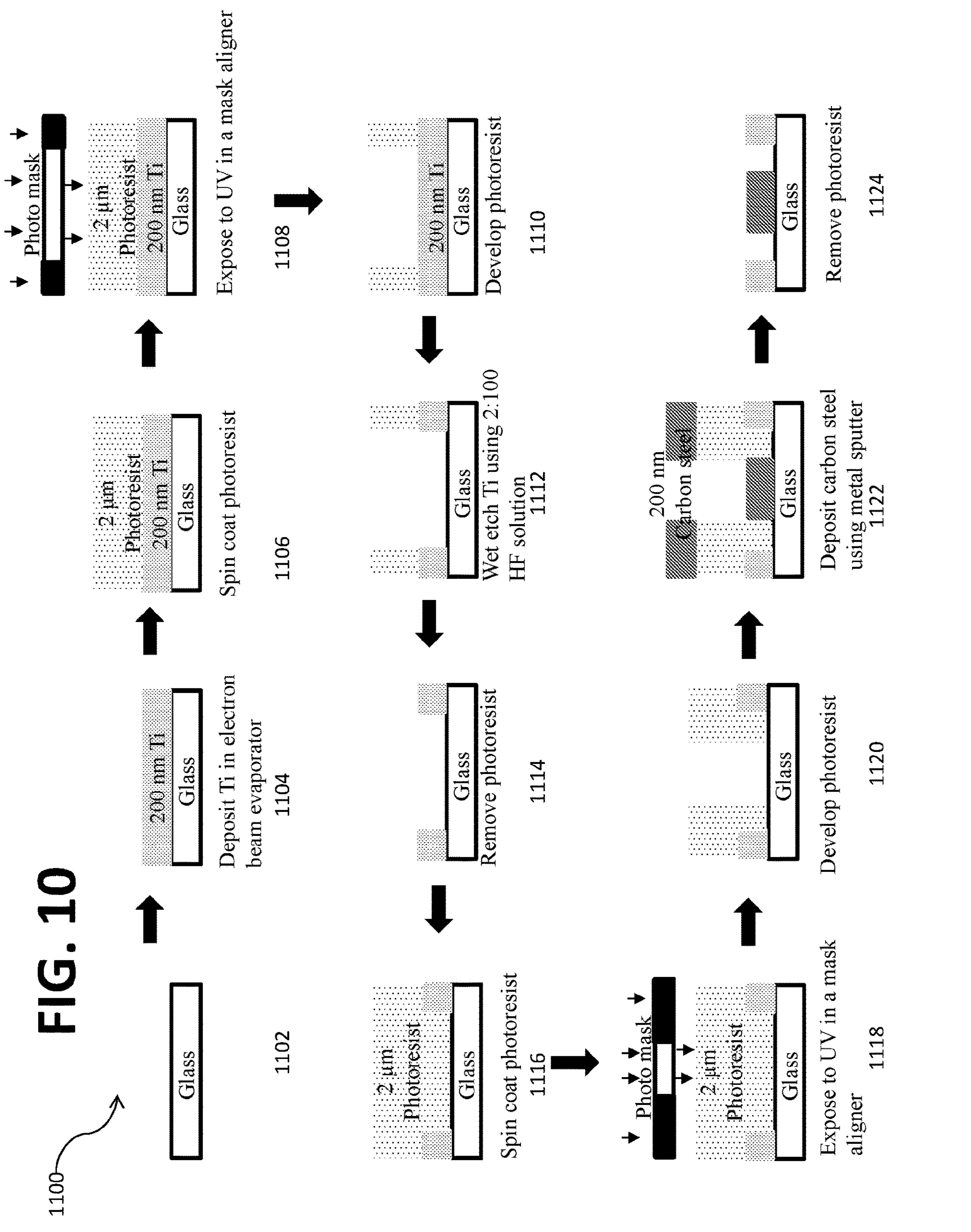
FIG. 10 is an example method 1100 of manufacturing an M-MIC according to certain embodiments of the present disclosure.

In an embodiment, the M-MIC comprises a glass slide with patterned metal electrodes, bonded to a polydimethylsiloxane (PDMS) microchannel structure. FIG. 10 is an example method 1100 of manufacturing the M-MIC. In an embodiment, prior to the method 1100, a silicone elastomer and a curing agent were mixed in a 10:1 ratio and poured onto a 3D printed mold with rectangular ridge structure (inverse of a microchannel structure) that are 1000 μm in width, 10 mm in length and 500 μm in height. The PDMS block was peeled after curing, resulting in an inverse replica of the mold structure, this structure is employed to form the channel discussed herein and shown at least in FIGS. 1-3. At block 1102, at least one borosilicate glass slide of about 2"×3" and 1.1 mm thick is pre-cleaned with piranha solution containing 4:1 vol/vol ratio of sulfuric acid and hydrogen peroxide for 10 minutes and with 1:100 HF solution for 30 s. At block 1104, a 200 nm-thick titanium electrode was deposited on borosilicate glass slide using a metal evaporator and the SAE 1018 carbon steel working electrode was deposited using metal sputtering (not shown here). In an embodiment, the width of each of the titanium and steel electrode metal layers was 0.45 mm and the gap between the two electrodes was about 0.1 mm. Patterning of the metal layers as described below to obtain the specific designs in FIGS. 1 and 2 was done using photolithography.

The photoresist S1818 was spin coated for 30 seconds at 4000 rpm at block 1106. A photoresist is a light-sensitive material that either dissolves in or is resistant to the dissolution in a solvent or etchant to aid in photolithography. S1818 is a positive photoresist and when exposed to UV dissolves in the appropriate etchant. The slides were then exposed to UV along with a photomask at block 1108 for 20 seconds based on the lamp intensity of 4 W/cm$^2$. To develop the photoresist at block 1110, the slides were developed in AZ 726 MIF solution for 45-60 seconds. The etching of titanium was done as shown at block 1112 using 2:100 solution of HF to DI water. The photoresist was removed at block 1114 by immersing the slides in acetone for 5 min.

After titanium was deposited, patterned and etched, a lift-off method was used to obtain the required pattern for steel. In the lift-off method, a photoresist pattern is used as a liftoff mold and disposed on the substrate at block 1116. At block 1118, a photomask is employed and the structure is exposed to UV in a mask aligner. The photoresist is then developed at block 1120 and then steel is sputtered at block 1122. Subsequently, at block 1124, the photoresist is dissolved and/or otherwise removed to obtain the steel electrode, completing the electrode pair of different materials. Subsequent to formation of the steel electrode, the patterned glass slide and PDMS layers discussed above are bonded to each other (not shown) by oxygen plasma treatment to form the M-MIC. In an embodiment, Tygon tubing of 0.01" inner diameter (ID)×0.03" outer diameter (OD) was used for all fluidic connections of inlets and outlets to the syringes. A syringe pump was used for obtaining continuous flow as shown in FIG. 4. Silver paste was used to attach copper wires of 24 gauge to the electrode pads for the first contact 306 and second contact 308 in FIG. 3, and epoxy was used to prevent the wires from subsequent unintentional detachment/decoupling.

While various embodiments have been shown and described, modifications thereof can be made by one skilled in the art without departing from the spirit and teachings of the disclosure. The embodiments described herein are exemplary only, and are not intended to be limiting. Many variations and modifications of the subject matter disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_L$ and an upper limit, $R_U$ is disclosed, any number falling within the range is specifically disclosed. In particular, the following numbers within the range are specifically disclosed: $R=R_L+V(R_U-R_L)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and methods are described in broader terms of “having”, “comprising,” “containing,” or “including” various components or steps, the compositions and methods can also “consist essentially of” or “consist of” the various components and steps. Use of the term “optionally” with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range are specifically disclosed. In particular, every range of values (of the form, “from about a to about b,” or, equivalently, “from approximately a to b,” or, equivalently, “from approximately a-b”) disclosed herein is to be understood to set forth every number and range encompassed within the broader range of values. Also, the terms in the claims have their plain, ordinary meaning unless otherwise explicitly and clearly defined by the patentee. Moreover, the indefinite articles “a” or “an”, as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A method for determining the susceptibility of a material to corrosion, the method comprising: generating, via an inlet in a monitoring device, a laminar flow of material comprising a plurality of microorganisms, wherein the plurality of microorganisms comprises at least one microorganism type; forming, inside the monitoring device, in response to the laminar flow, a biofilm comprising the at least one microorganism type; and applying a voltage to the first and second electrodes during the laminar flow.

B: A monitoring device for monitoring microbiologically influenced corrosion, the monitoring device comprising: a first electrode disposed parallel to a second electrode on a substrate; a top structure disposed over the first and second electrodes on the substrate; and a fluid channel formed between the first electrode, the second electrode, and the top structure, wherein the fluid channel comprises a first side and a second side.

C: A monitoring device for monitoring microbiologically influenced corrosion, the monitoring device comprising: an electrode disposed on a substrate; and a top structure disposed over the electrode on the substrate to form a channel, wherein the electrode comprises carbon steel, and wherein the channel extends from an inlet to an outlet and is configured to establish a laminar flow.

Each of embodiments A, B, and C may have one or more of the following additional elements: Element 1: wherein the monitoring device comprises a first side and a second side, and a first electrode configured parallel to a second electrode such that a fluid path where the laminar flow is generated extends from the first side to the second side. Element 2: wherein the first electrode and the second electrode comprise titanium. Element 3: wherein the first electrode and the second electrode comprise steel. Element 4: wherein the first electrode comprises titanium and the second electrode comprises steel. Element 5: wherein the fluid path extending from the first side to the second side is microfluidic, having a dimension along a direction of fluid flow from the first side to the second side is at least ten times a dimension of the fluid path in a direction perpendicular to the fluid flow from the first side to the second side, and wherein the dimension of the fluid path in the direction perpendicular to the fluid flow is less than or equal to about 1000 μm. Element 6: wherein generating the laminar flow comprises establishing a flow rate of the material from about 0.1 mL/h to about 2 mL/h. Element 7: further comprising, subsequent to applying the voltage, determining an impedance variation. Element 8: further comprising capturing an image of the biofilm using a confocal microscope. Element 9: further comprising an inlet coupled to the first side of the fluid channel and a syringe pump coupled to the inlet. Element 10: wherein the substrate comprises glass. Element 11: wherein the top structure comprises a gas-permeable polymer. Element 12: wherein the top structure is optically transparent. Element 13: wherein the gas-permeable polymer comprises polydimethylsiloxane (PDMS). Element 14: wherein the channel or fluid channel is microfluidic, having a dimension along a direction of fluid flow from the first side to the second side that is at least ten times a dimension of the fluid channel in a direction perpendicular to the fluid flow from the first side to the second side, and wherein the dimension of the fluid channel in the direction perpendicular to the fluid flow is less than or equal to about 1000 μm. Element 15: further comprising a power source coupled to the electrode. Element 16: further comprising a pump coupled to the inlet.

While preferred embodiments of the invention have been shown and described, modifications thereof can be made by one skilled in the art without departing from the teachings of this disclosure. The embodiments described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference. Unless expressly stated otherwise, the steps in a method claim may be performed in any order and with any suitable combination of materials and processing conditions.

What is claimed is:

1. A device for monitoring microbiologically influenced corrosion, the device comprising:

- a microbiologically influenced corrosion (MIC) apparatus comprising:
  - a single electrode disposed directly on a substrate, wherein the substrate comprises glass;
  - a top structure disposed over the single electrode on the substrate to form a channel in a negative space between the single electrode on the substrate and the top structure, wherein the single electrode comprises carbon steel, and wherein the channel extends from an inlet to an outlet and is configured to establish a laminar flow therein at a flow rate of from 0.10 mL/h to 2 mL/h;
- a power source coupled to the single electrode, wherein the power source is configured as a potentiostat for applying an alternating current voltage signal to the single electrode and measuring impedance variations to determine corrosion of the single electrode during biofilm formation;
- a pump coupled to the inlet;
- a confocal microscope; and
- an incubator configured to control a temperature of the MIC apparatus, wherein the MIC apparatus, the pump, and at least a portion of the confocal microscope are disposed within the incubator.

2. The device of claim 1 further comprising, a base on which the MIC apparatus rests, wherein the confocal microscope is removably coupled to the base.

3. The device of claim 1, wherein the channel is microfluidic, having a dimension along a direction of fluid flow from the inlet to the outlet that is at least ten times a dimension of the channel in a direction perpendicular to the fluid flow from the inlet to the outlet, and wherein the dimension of the channel in the direction perpendicular to the fluid flow is less than or equal to about 1000 μm.

4. The device of claim 1, wherein the channel is microfluidic, having a dimension along a direction of fluid flow from the inlet to the outlet that is at least ten times each of a width of the channel in a first direction perpendicular to the fluid flow from the inlet to the outlet and a height of the channel in a second direction perpendicular to the fluid flow from the inlet to the outlet.

5. The device of claim 4, wherein the width of the channel in the first direction perpendicular to the fluid flow is less than or equal to about 5000 μm.

6. The device of claim 4, wherein the width of the channel in the first direction perpendicular to the fluid flow is less than or equal to about 2000 μm.

7. The device of claim 4, wherein the width of the channel in the first direction perpendicular to the fluid flow is less than or equal to about 1000 μm.

8. The device of claim 4, wherein the height of the channel in the second direction perpendicular to the fluid flow is less than or equal to about 1000 μm.

9. The device of claim 4, wherein the height of the channel in the second direction perpendicular to the fluid flow is less than or equal to about 500 μm.

10. The device of claim 4, wherein the top structure comprises polydimethylsiloxane (PDMS).

11. The device of claim 4, wherein the carbon steel comprises 1018 grade carbon steel.

* * * * *